United States Patent [19]

Beversdorf et al.

[11] Patent Number: 4,517,763
[45] Date of Patent: May 21, 1985

[54] HYBRIDIZATION PROCESS UTILIZING A COMBINATION OF CYTOPLASMIC MALE STERILITY AND HERBICIDE TOLERANCE

[75] Inventors: Wallace D. Beversdorf; Lawrence R. Erickson; Ian Grant, all of Guelph, Canada

[73] Assignee: University of Guelph, Guelph, Canada

[21] Appl. No.: 493,511

[22] Filed: May 11, 1983

[51] Int. Cl.³ .................... A01B 79/00; A01H 5/02
[52] U.S. Cl. .................................. 47/58; 47/DIG. 1
[58] Field of Search .................. 47/1 R, 1.5, 1.7, 58, 47/DIG. 1

[56] References Cited

U.S. PATENT DOCUMENTS

| 4,045,912 | 9/1977 | Sun | 47/58 |
|---|---|---|---|
| 4,351,130 | 9/1982 | Rutger et al. | 47/58 |
| 4,443,971 | 4/1984 | Chaleff | 47/58 |

OTHER PUBLICATIONS

Faulkner, G. S. (1982) Chapter 12: "Breeding Herbicide-Tolerant Crop Cultivars by Conventional Methods", *Herbicide Resistance in Plants*, Pub. John Wiley & Sons, Inc., pp. 235-256.
D. E. Falk, K. J. Kash, and E. Reinbergs, Proceedings of the Fourth International Barley Genetics Symposium, Edinburgh, Jul. 22 to 29, 1981 (Edinburgh University Press), pp. 778 to 785.
Registration of a Shrunken Endosperm, Male-Sterile Germplasm to Facilitate Hybridization in Barley (Reg No. GP 59), D. E. Falk and K. J. Kasha, Crop Science vol. 22, Mar.-Apr. 1982, p. 450.
Highlights of Agriculture Research in Ontario, Dec. 1982, at pp. 18-19 in an article by W. D. Beversdorf and David J. Hume entitled "Canola: A New Oilseed Crop for Ontario."
Ontario Ministry of Agriculture and Food Factsheet No. 82-017, Feb. 1982, entitled "Spring Canola in Ontario" by D. J. Hume, R. J. McLaughlin, and W. D. Beversdorf.
I. Bartkowiak-Broda, P. Rousselle, and M. Renard (1979), "Investigation of Two Kinds of Cytoplasmic Male Sterility in Rape (*Brassica napus*, L.)", Genet. Polon. 20:487-497.
Y. Ohkawa, T. Shiga, and T. Ishige (1979), "Male Sterility-Inducing-Cytoplasm in *Brassica campestris* var. *rapifera*", Annual Report, Division of Genetics, Dept. of Physiol. and Genetics, Nat. Inst. of Agric. Sciences, Kannondai, Yatabe, Tsukuba, Japan, pp. 30-31.
J. D. Palmer, C. R. Shields, D. B. Cohen, and T. J. Orton (1983), "An Unusual Mitochrondrial DNA Plasmid in the Genus Brassica", Nature 301:725-728.
P. Rousselle and M. Renard (1982), "Interet du cultivar 'Bronowski' pour l'obtention de plantes male-steriles cytoplasmiques chez le colza (*Brassica napus* L.)", Agronomie 2 (10):951-956.
T. Shiga (1976), "Studies on Heterosis Breeding Using Cytoplasmic Male Sterility in Rapeseed, *Brassica napus* L.," Bull. Nat. Inst. Agric. Sci. Tokyo Series D, 27:75-85.
T. Shiga (1976), "Cytoplasmic Male Sterility and Its Utilization for Heterosis Breeding in Rapeseed, *Brassica napus* L.," JARQ 10:177-182.
T. Shiga (1980), "Male Sterility and Cytoplasmic Differentiation," Chapter 12 in Brassica Crops and Wild Allies-Biology and Breeding, Japan Sci. Soc. Press, Tokyo, pp. 205-221.
K. F. Thompson (1972), "Cytoplasmic Male-Sterility in Oil-Seed Rape," Heredity 29(2):253-257.
F. Vedel, C. Mathieu, P. Lebacq, F. Ambard-Bretteville, and R. Remy (1982), "Comparative Macromolecular Analysis of the Cytoplasms of Normal and Cytoplasmic Male Sterile *Brassica napus*," Theor. Appl. Genet. 62:255-262.
"Transfer of Cytoplasmically-Inherited Triazene Resistance from Bird's Rape to Cultivated Oilseed Rape (*Brassica campestris* and *B. napus*)," by W. D. Beversdorf, J. Weiss-Lerman, L. R. Erickson, and V. Souza Machado appearing in the Canadian Journal of Genetics and Cytology, vol. XXII, No. 2, Jun., 1980, pp. 167-172.

(List continued on next page.)

*Primary Examiner*—James R. Feyrer
*Attorney, Agent, or Firm*—Burns, Doane, Swecker & Mathis

[57] ABSTRACT

The process of the present invention provides a convenient route for producing a predetermined hybrid variety of a crop which is capable of undergoing both self-pollination and cross-pollination. Cytoplasmic male sterile plants which also exhibit cytoplasmic herbicide tolerance are the key plants for use in the present process. Such cytoplasmic male sterile plants may be readily multiplied and uniformly produced in accordance with the process of the present invention on a relatively economical basis by crossing with suitable maintainer plants. Economical bulk planting of the key plants with either maintainer or restorer plants is made possible. Following cross-pollination from a pollen source which lacks the herbicide tolerance unneeded plants effectively are eliminated by use of a herbicide. For instance, unwanted plants may be effectively eliminated immediately after pollination or prior to pollination in a succeeding generation to make possible the existence in an unharmed state of a substantially homogeneous stand of the desired plants which exhibit cytoplasmic herbicide tolerance. The process of the present invention is applicable to grain crops, forage crops, seed propagated fruits, seed propagated ornamentals, and industrial species. In a particularly preferred embodiment a predetermined variety of *Brassica napus* (i.e., rape or improved forms thereof known as canola) is formed which is the product of cross-pollination.

34 Claims, No Drawings

OTHER PUBLICATIONS

"Uniparental Inheritance of Chloroplast Atrazine Tolerance in *Brassica Campestris*" by V. Souza Machado, J. E. Bandeen, G. R. Stephenson, and P. Lavigne, Can. J. Plant Sci. 58:977-981, 1978.

"Registration of Triazine Resistant *Brassica napus* Germplasm" (Reg. No. GP 2), W. D. Beversdorf, J. Weiss-Lerman, and L. R. Erickson, Crop Science, vol. 20, Mar.-Apr., 1980, p. 289.

1980 Germ Plasm Releases, Crop Science Department, Ontario Agricultural College, University of Guelph.

1983 Germ Plasm Releases, Crop Science Department, Ontario Agricultural College, University of Guelph.

HYBRIDIZATION PROCESS UTILIZING A COMBINATION OF CYTOPLASMIC MALE STERILITY AND HERBICIDE TOLERANCE

BACKGROUND OF THE INVENTION

Plant scientists have recognized for many years that the hybridization of closely related plants may result in the production of offspring having a combination of desirable traits which previously were possessed separately by the parent plants. Also hybrid plants of various crops commonly have possessed a vigor or heterosis which has contributed significantly to the crop yield and accordingly has been of considerable economic importance.

Since the plants selected for hybridization studies commonly are capable of undergoing both self-pollination and cross-pollination, the desired crossing often has been difficult to achieve on a reliable basis while operating on a commercially viable scale. Accordingly, controlled cross-pollination must be achieved in the substantial absence of self-pollination. A common technique heretofore utilized to accomplish this goal has been the use of cytoplasmic male sterile plants as the seed parent which are grown as a substantially uniform population adjacent another substantially uniform population of plants from which the pollen is derived. Such technique has required precise control of the planting patterns, sufficient pollen transfer from one block of plants to another, and precise control of the seed harvest to preclude comingling of the two different seed products which are produced.

In U.S. Pat. No. 3,842,538 is disclosed a method of hybrid seed grain production wherein the bulk planting of cytoplasmic male sterile parent and the pollen parent is proposed. The seeds capable of forming hybrid plants are thereafter separated from the non-hybrid seeds on the basis of color. Such seed separation technique still would be tedious; however, and is not believed to have been commercially adopted. See also, articles by D. E. Falk, K. J. Kasha, and E. Reinbergs appearing in Proceedings of the Fourth International Barley Genetics Symposium, Edinburgh, July 22 to 29, 1981 (Edinburgh University Press) pages 778 to 785, and by D. E. Falk and K. J. Kasha appearing in Crop Science, Vol. 22, March–April, 1982, page 450, where a tight linkage between genetic male sterility and a shrunken endosperm is discussed.

While considerable success has been realized in the past through the adoption of various well-known hybridization techniques, the need nevertheless has remained for alternate less tedious, more efficient, or otherwise improved hybridization routes. Additionally, for many crops commercially feasible hybridization technology is yet to be implemented in spite of continuing research by dedicated plant scientists working around the world.

An example of a crop which is yet to benefit from the commercial availability of seed capable of growing hybrid plants is rape (i.e., *Brassica napus* or *Brassica campestris*). While not necessarily recognized by the general public, rape (and particularly high quality forms thereof known as canola) is being grown as an increasingly important oilseed crop and a source of rapeseed meal in many parts of the world. The oil may serve as a high quality vegetable oil and the meal may be used as a nutritious protein concentrate for livestock. The importance of rape as an agronomic crop is discussed in (1) Highlights of Agricultural Research in Ontario, December 1982, at Pages 18–19 in an article by W. D. Beversdorf and David J. Hume entitled "Canola: A New Oilseed Crop for Ontario", and in (2) the Ontario Ministry of Agriculture and Food Factsheet No. 82-017, February 1982, entitled "Spring Canola in Ontario" by D. J. Hume, R. J. McLaughlin and W. D. Beversdorf.

Representative publications of researchers working in the area of rapeseed technology who have identified cytoplasmic male sterility in rape plants are identified below:

Bannerot, H., Boulidard, I., Cauderon, Y., and Tempe, J. (1974). "Cytoplasmic Male Sterility Transfer From Raphanus to Brassica." Proc. Eucarpia Meeting Cruciferae Vegetable Crop., Sect. 25:52–54.

Bartkowiak-Broda, I., Rousselle, P., and Renard, M. (1979). "Investigation of Two Kinds of Cytoplasmic Male Sterility in Rape (*Brassica napus* L.)". Genet. Polon. 20:487–497.

Ohkawa, Y., Shiga, T., and Ishige, T. (1979). "Male Sterility-Inducing-Cytoplasm in *Brassica campestris* var. *rapifera*", Annual Report, Division of Genetics, Dept. of Physiol. and Genetics, Nat. Inst. of Agric. Sciences, Kannondai, Yatabe, Tsukuba, Japan, Pages 30–31.

Palmer, J. D., Shields, C. R., Cohen, D. B., and Orton, T. J. (1983). "An Unusual Mitochondrial DNA Plasmid in the Genus Brassica". Nature 301:725–728.

Rousselle, P., and Renard, M. (1982) "Intérêt du cultivar <<Bronowski>> pour l'obtention de plantes mâle-stériles cytoplasmiques chez le colza (*Brassica napus* L.)" Agronomie 2 (10):951–956.

Shiga, T. (1976). "Studies on Heterosis Breeding Using Cytoplasmic Male Sterility in Rapeseed. *Brassica napus* L.", Bull. Nat. Inst. Agric. Sci. Tokyo Series D. 27:75–85.

Shiga, T. (1976). "Cytoplasmic Male Sterility and Its Utilization for Heterosis Breeding in Rapeseed, *Brassica napus* L.", JARQ 10:177–182.

Shiga, T. (1980). "Male Sterility and Cytoplasmic Differentiation". Chapter 12 in Brassica Crops and Wild Allies-Biology and Breeding. Japan Sci. Soc. Press, Tokyo, Pages 205–221.

Thompson, K. F. (1972). "Cytoplasmic Male-Sterility in Oil-Seed Rape". Heredity 29(2):253–257.

Vedel, F., Mathieu, C., Lebacq, P., Ambard-Bretteville, F., and Remy, R. (1982). "Comparative Macromolecular Analysis of the Cytoplasms of Normal and Cytoplasmic Male Sterile *Brassica napus*". Theor. Appl. Genet. 62:255–262.

It has also been recognized in the past that weed control is an important consideration for those who choose to grow rape. Unchecked weeds will lessen the ultimate yield and can significantly reduce the quality by unavoidable contamination from diverse seeds which are harvested along with the desired crop. In order to deal with the weed problem various herbicide tolerant varieties of rape have been proposed so that unwanted weeds can be efficiently eliminated while growing in close proximity to the rape plants. See in this regard, "Transfer of Cytoplasmically-Inherited Triazine Resistance From Bird's Rape to Cultivated Oilseed Rape (*Brassica campestris* and *B. napus*)", by W. D. Beversdorf, J. Weiss-Lerman, L. R. Erickson and V. Souza Machado appearing in the Canadian Journal of Genetics and Cytology, Volume XXII, No. 2, June 1980, Pages 167–172. See also "Uniparental Inheritance of Chloroplast Atrazine Tolerance in Brassica Campestris" by V. Souza Machado, J. D. Bandeen, G. R. Stephenson and P. Lavigne, Can. J. Plant Sci. 58:977–981, 1978.

It is an object of the present invention to provide an improved hybridization process for use in forming a predetermined hybrid variety of a crop which is capable of undergoing both self-pollination and cross-pollination.

It is an object of the present invention to provide an improved hybridization process for use in forming a predetermined hybrid variety of a crop which is capable of undergoing both self-pollination and cross-pollination wherein the seed-parent is cytoplasmic male sterile and wherein the pollen parent conveniently may be grown in bulk with the seed parent during at least one step of the process without the need for a precise planting pattern and the disadvantages associated therewith.

It is an object of the present invention to provide an improved hybridization process for use in forming a predetermined hybrid variety of a crop wherein the cross-fertilization of cytoplasmic male sterile plants with maintainer plants readily may be accomplished.

It is an object of the present invention to provide an improved hybridization process for use in forming a predetermined hybrid variety of a crop which is capable of undergoing both self-pollination and cross-pollination wherein the desired product may be formed on a reliable basis.

It is an object of the present invention to provide an improved hybridization process for use in forming a predetermined variety of a crop which is capable of undergoing both self-pollination and cross-pollination which is suitable for utilization on an economical basis on a commercially attractive scale.

It is an object of the present invention to provide an improved hybridization process for use in forming a predetermined variety of a crop which is capable of undergoing both self-pollination and cross-pollination wherein the desired product additionally exhibits herbicide tolerance which makes possible the selective destruction with ease of troublesome weeds growing within the hybrid crop area.

It is an object of the present invention to provide an improved hybridization process which particularly is suited for use when forming a predetermined variety of rape (e.g., *Brassica napus*), and to thereby provide a commercially practicable route for forming hybrid rape.

It is a further object of the present invention to provide a new and useful *Brassica napus* seed product which is suitable for use when carrying out the process of the present invention.

These and other objects and advantages will be apparent to those skilled in the art from a reading of the following description and appended claims.

SUMMARY OF THE INVENTION

It has been found that an improved process for forming a substantially homogeneous population of plants of a predetermined hybrid variety of a crop which is capable of undergoing both self-pollination and cross-pollination comprises:

(a) growing in a first planting area a substantially random population of (1) cytoplasmic male sterile plants which exhibit cytoplasmic herbicide tolerance, and (2) male fertile plants which are capable of pollinating the cytoplasmic male sterile plants and which lack cytoplasmic herbicide tolerance, whereby the cytoplasmic male sterile plants (1) and the male fertile plants (2) are pollinated with pollen derived from the male fertile plants and seed is formed on the cytoplasmic male sterile plants and on the male fertile plants, (b) harvesting in bulk the seed which is formed on the plants of the first planting area, (c) growing at least a portion of the seed from step (b) in a second planting area in the absence of segregation between the seed derived from the cytoplasmic male sterile plants which exhibit cytoplasmic herbicide tolerance and the male fertile plants which lack cytoplasmic herbicide tolerance, and (d) contacting substantially all of the plants present in the second growing area prior to pollination with a herbicide which is effective to destroy the plants resulting from seed formed on the male fertile plants of the first planting area, whereby a substantially homogeneous population of a predetermined hybrid variety is formed which resulted from seed formed on the male sterile plants of the first planting area.

Alternatively, it has been found that an improved process for producing seed capable of forming a predetermined hybrid variety of a crop which is capable of undergoing both self-pollination and cross-pollination comprises:

(a) growing in a planting area a substantially random population of (1) cytoplasmic male sterile plants which exhibit cytoplasmic herbicide tolerance, and (2) male fertile plants which are capable of pollinating the cytoplasmic male sterile plants and which lack cytoplasmic herbicide tolerance, whereby the cytoplasmic male sterile plants (1) are pollinated with pollen derived from the male fertile plants (2), (b) contacting substantially all of the plants present in the growing area following the pollination with a herbicide which is effective to destroy the male fertile plants and which is ineffective to destroy the cytoplasmic male sterile plants, and (c) harvesting seed from the cytoplasmic male sterile plants which is capable of forming the hybrid plants in the substantial absence of seed from the male fertile plants which initially grew in the planting area.

The key composition of matter for use in a preferred embodiment of the process of the present invention is a *Brassica napus* seed product consisting of a substantially homogeneous assemblage of seeds which upon growth yield rape plants which exhibit a combination of cytoplasmic male sterility and cytoplasmic atrazine tolerance when applied as a foliar spray at a rate of 2 kilograms per hectare.

Another important composition of matter in accordance with a preferred embodiment of the concept of the present invention is a *Brassica napus* seed product consisting of a substantially homogeneous binary admixture of seeds which upon growth yield (1) a first rape plant component which exhibits cytoplasmic male sterility and cytoplasmic atrazine tolerance when applied as a foliar spray at a rate of 2 kilograms per hectare, and (2) a second rape plant component which is capable of pollinating the first rape plant component, is a homozygous recessive maintainer for the cytoplasmic male sterility of the first rape plant component, and which lacks atrazine tolerance when applied as a foliar spray at a rate of 2 kilograms per hectare.

Yet another important composition of matter in accordance with a preferred embodiment of the concept of the present invention is a *Brassica napus* seed product consisting of a substantially homogeneous binary admixture of seeds which upon growth yield (1) a first rape plant component which exhibits cytoplasmic male sterility and cytoplasmic atrazine tolerance when applied as a foliar spray at a rate of 2 kilograms per hectare, and (2) a second rape plant component which is capable of pollinating the first rape plant component, is a homozygous dominant fertility restorer for said first rape plant component, and which lacks atrazine tolerance when applied as a foliar spray at a rate of 2 kilograms per hectare.

DESCRIPTION OF PREFERRED EMBODIMENTS

The hybridization concept of the present invention is deemed to be generally applicable for the formation of a predetermined variety of any crop which is capable of undergoing both self-pollination and cross-pollination. For the purposes of the present invention hybridization is deemed to occur when two parent plants are cross-pollinated which are not identical from the nuclear and cytoplasmic point of view. Accordingly, seed capable of forming a hybrid plant is deemed to result following the fertilization of a cytoplasmic male sterile plant with pollen from either a maintainer or a restorer plant which is capable of pollinating the same.

A predetermined hybrid variety of a grain crop, a forage crop, a seed propagated fruit, a seed propagated ornamental, or of an industrial species, etc. may be formed in accordance with the process of the present invention. For the purposes of the present invention grain crops are those which are grown primarily for seed, and forage crops are those which are grown primarily for the consumption of plant parts other than seed such as the foliage or other vegatative structure.

Representative grain crops which may be hybridized in accordance with the process of the present invention include cereals (e.g., wheat, oats, barley, rye, corn, triticale, sorghum, etc.), grain legumes (e.g., field beans, peas, peanuts, lentils), and oilseeds (e.g., flax, mustard, safflower, sunflowers, soybeans, rape, etc.). Representative forage crops which may be hybridized in accordance with the process of the present invention include alfalfa, sugar beets, onions, peppers, seed propagated potatoes, turnips, cabbage, broccoli, brome grass, etc. Representative seed propagated fruits which may be hybridized in accordance with the process of the present invention include tomatoes, peppers, watermelons, etc. Representative seed propagated ornamentals which may be hybridized in accordance with the process of the present invention include petunias, marigolds, etc. Representative industrial species which may be hybridized in accordance with the process of the present invention include poplar trees, maple trees, cotton, fibre flax, tobacco, kelp, etc.

The process of the present invention is particularly suited for the formation of a hybrid variety of a crop of the family Brassicaceae, which is sometimes designated the Cruciferae family or the Mustard Family. Within this family one may select with greater particularity a crop of the genus Brassica (e.g., a hybrid variety of rape plant classified as *Brassica napus* or *Brassica campestris*). Each of these previously named species occurs in a spring and winter (fallseeded) type. High quality forms of rapeseed which are used primarily as a source of vegetable oil and of rapeseed meal (a protein concentrate for livestock) are commonly referred to as canola. For instance, canola often identifies quality rapeseed which is low in erucic acid (less than 5%) and glucosinolates (less than 3 milligrams per gram of oil-free meal). Alternatively, rapeseed may be employed in the production of lubricants, paints, varnishes, and plastics in accordance with known technology.

When carrying out the process of the present invention it is necessary to select a potential parent plant which exhibits a combination of cytoplasmic male sterility and cytoplasmic herbicide tolerance. A parent plant is selected by known techniques wherein the cytoplasm possesses both of these prerequisites. Accordingly, the male sterility and herbicide tolerance must be manifest because of the specific type of cytoplasm which is inherently present. It further commonly is essential when forming grain crops that the cytoplasmic male sterile plant possess the ability to form seed which yields fully fertile hybrid plants following pollination from a pollen source which possesses homozygous dominant fertility restoring genes which are capable of interacting with the cytoplasm. The cytoplasmic male sterile plant will possess the ability to form seed which yields cytoplasmic male sterile plants following pollination from a pollen source which lacks the dominant fertility restoring genes. There is no requirement that the cytoplasmic herbicide tolerance be incapable of transmission to a succeeding generation. In fact it is preferred that the cytoplasmic herbicide tolerance not be influenced under any circumstances by the genes introduced from the pollen source.

For the purposes of the present invention a plant is considered to be male sterile when it is incapable of dehiscing functional pollen (i.e., is incapable of in situ fertilization of an egg).

For the purposes of the present invention a plant is considered to possess cytoplasmic herbicide tolerance when its abilitY to withstand or to endure a given herbicide while carrying on its normal plant functions (e.g., seed formation)can be traced to the nature of the cytoplasm of the plant. In contrast plants which lack such herbicide tolerance are significantly impaired or otherwise destroyed under the same conditions. Such lack of herbicide tolerance also can be manifest through the prevention of seed germination whereby the potential plant is destroyed at a very early stage in its development.

The mode of operation of the particular herbicide employed in the process of the present invention can be varied widely so long as the required elimination of unwanted plants can be selectively accomplished without undue damage to the cytoplasmic herbicide tolerant plants at the appropriate stage in the process. A herbicide should be employed which is recognized to be safe for agricultural use. For instance, it has been found that known agricultural herbicides which operate by inhibiting photosynthesis may be selected. However, herbicides which function by other routes likewise may be selected so long as the desired controlled elimination of unwanted plants can be accomplished. Representative classes of suitable herbicides are the s-triazines and the as-triazines. In a preferred embodiment with rape the herbicide is atrazine (i.e., 2-chloro-4-ethylamino-6-isopropylamino-s-triazine). Alternatively, other representative herbicides for use with rape are cyanazine (i.e., [[4-chloro-6-(ethylamino)-s-triazine-2-yl]amino]-2- methylpriionitrile) and metribuzin (i.e., 4-amino-6-tert-butyl-3-(methylthio)-as-triazine-5(4H)-one).

The herbicide can be applied by conventional means prior to pollination or after pollination. Prior to pollination the herbicide may be applied to seeds at the pre-emergence stage so as to prevent germination or to the young seedling plants at the post-emergence stage following germination. Alternatively, the herbicide may be applied to older plants. The herbicide may be applied to the entire plant or to plant parts, such as to the roots through the soil, to the leaves, to the stems, etc. For instance, when using atrazine as the herbicide with rape, the herbicide conveniently may be applied as an aqueous foliar spray to the leaves and stems of the growing plants at a rate of approximately 0.5 to 4 kilograms per hectare (e.g., approximately 2 kilograms per hectare). The 2 kilograms per hectare rate of application of atrazine to *Brassica napus* plants has been found to be a safe and effective rate; however, a lesser application rate frequently may be used. A conventional emulsifier or oil optionally also may be present at the time of application. Alternatively, the herbicide may be applied as solid granules directly to the plant or to the soil as will be apparent to those skilled in herbicide use.

It has been found that the key plant for use in the process of the present invention may be selected or derived from plants which have been subjected to a herbicide for an extended period of time, preferably for a number of generations. The natural selection process which has been found to occur in such surviving plants effectively leads plant researchers to those individual plants which inherently possess the requisite herbicide tolerance. Subsequent testing can be employed to clearly identify those individual plants which possess the requisite herbicide tolerance and in which such tolerance can be attributed to the cytoplasm and not exclusively to nuclear factors which are transmitted through the pollen. During the selection process it is possible also to examine plants which are related but not in all respects analogous to the plant which is sought to be hybridized.

Once plants having the requisite cytoplasmic herbicide tolerance are on hand, populations of these can be pollinated in a wide hybridization plant breeding program and observed and selected for those which dehisce no functional pollen. Via this route one may obtain the required plants which exhibit the combination of cytoplasmic male sterility and cytoplasmic herbicide tolerance. Since it has been found that the same cytoplasm is involved for each the search for the requisite male sterility greatly is simplified.

Other techniques which may be employed to yield the key plant for use in the present invention include the controlled introgression of the recessive genes for fertility restoration from available male steriles into the nucleus of a herbicide tolerant line. Recently available biotechnology techniques may be employed such as protoplast fusion involving a herbicide tolerant line and a cytoplasmic male sterile line, organelle transformation, and DNA transformation wherein both organelle and nuclear DNA are modified. Also, the mutagenesis of the cytoplasmic genome of the herbicide tolerant line may be accomplished. Once the key plant having both cytoplasmic herbicide tolerance and cytoplasmic male sterility is located or synthesized, tissue culture may be employed to multiply it so that its characteristics can be confirmed on a larger scale.

Maintainer plants which are capable of pollinating the plants which exhibit cytoplasmic male sterility and cytoplasmic herbicide tolerance must, by necessity, be homozygous maintainers with respect to recessive fertility restorer genes which interact with the requisite cytoplasm. They also must lack cytoplasmic herbicide tolerance with respect to the same herbicide which can be tolerated by cytoplasmic male sterile and cytoplasmic herbicide tolerant plants. Suitable maintainer plants can be developed simultaneously with the search for the cytoplasmic male sterile plants since they commonly are necessary in order to easily confirm whether the desired cytoplasm is in fact present. The maintainer plant selected commonly possesses substantially the same nuclear genotype as the cytoplasmic male sterile plant with the exception of the cytoplasm. Controlled introgression of the recessive genes for fertility restoration from partial male steriles into fertile cytoplasms may be accomplished. Such partial male steriles are heterozygous since only one half of the gametes produced are recessive for the fertility restoration gene. Male parents which have been found to induce cytoplasmic male sterility following wide hybridization may be tested for the presence of recessive genes for fertility restoration. Also, naturally recurring populations or currently grown cultivars may be evaluated by known techniques for the presence of recessive genes for fertility restoration. The agronomic properties of the key plants may be improved through well known backcross techniques. The progeny of a cross between the cytoplasmic male sterile plant and the maintainer plant are always cytoplasmic male sterile, and also cytoplasmic herbicide tolerant.

Restorer plants which are capable of pollinating the plants which exhibit cytoplasmic male sterility and cytoplasmic herbicide tolerance are readily available and require little investigation in order to locate. These plants must, by necessity, be homozygous restorers with respect to the dominant fertility restorer genes which interact with the requisite cytoplasm. Because of the dominant transmission mode these plants often are far more common than the maintainer plants in a given plant population. Such restorer plants lack cytoplasmic herbicide tolerance with respect to the same herbicide as the cytoplasmic male sterile plants which also exhibit cytoplasmic herbicide tolerance.

The article appearing in the Canadian Journal of Genetics and Cytology, Volume XXII, No. 2, June 1980, by W. D. Beversdorf, J. Weiss-Lerman, L. R. Erickson and V. Souza Machado entitled "Transfer of Cytoplasmically-Inherited Triazine Resistance from Bird's Rape to Cultivated Rape (*Brassica campestris* and *B. napus*)" discusses a route whereby one may obtain cytoplasmic tolerance for a herbicide in the named plants of agronomic importance. More specifically, it initially was observed that a weed biotype of *Brassica campestris* known as bird's rape infested a corn field near Brampton, Quebec, Canada, in spite of prolonged applications of conventional triazine herbicides. Accordingly, this weed biotype was deemed to be tolerant to at least seven s-triazine herbicides including atrazine as described. This triazine tolerance through controlled backcrossing techniques was transferred to known cultivars of oilseed rape (i.e., *Brassica campestris* and *Brassica napus*) to provide improved oilseed rape cultivars which could be used in weed control programs. More specifically, during flowering crosses were made between emasculated flowers of bird's rape and oilseed rape cultivars (e.g., Tower cultivar). It was found that all backcross progeny from (bird's rape X cultivar) X cultivar were resistant to an application of atrazine while all backcross progeny from (cultivar X bird's rape) X cultivar were killed by the atrazine application, as were the cultivar controls. The results accordingly indicated that the atrazine resistance had been cytoplasmically inherited.

Samples of the resulting herbicide tolerant *Brassica napus* seed previously have been released to the public by the Crop Science Department, Ontario Agricultural College, University of Guelph, Ontario, Canada, under the designation of Reg. No. GP 2, and Catalogue No. ATR-5Tw in its 1980 and 1983 Germ Plasm Releases. In this regard also see "Registration of Triazine Resistant *Brassica Napus* Germplasm" which appeared in Crop Science, Vol. 20, March-April 1980, page 289. Also, herbicide tolerant *Brassica napus* seed from this program has been deposited in the National Seed Storage Laboratory at Fort Collins, Colorado, USA under our Sample No. ATR-5Tw, Laboratory Assession No. BNa-21, and Ser. No. 180,171. Such seed identified above is capable of growing plants which are all fully male fertile. It was contemplated that the use of seed having such herbicide tolerance would enable the growing of a commercial rape crop in which weeds such as stinkweed (*Thlaspi arvense*, L.) and wild mustard (*Brassica haber* D. C. Wheeler) could be readily eliminated without harm to the commercial crop.

We have subsequently discovered that rape plants which possess cytoplasmic herbicide tolerance may be developed from ATR-5Tw which possess the requisite cytoplasmic male sterility for use in the process of the present invention. This was accomplished by crossing such *Brassica napus* cytoplasmic herbicide tolerant rape backcrosses while serving as the female parent with pollen from a male parent of a cultivar of *Brassica napus* such as Bronowski, which has been found to be highly variable with respect to recessive genes for fertility restoration, and subsequently carrying out enforced selfing to the $F_2$ generation. The $F_2$ plants which exhibited reduced male fertility were next visually selected and isolated. Such plants were partially male sterile and were heterozygous with respect to the genes for fertility restoration. Enforced self-pollination of the partially male sterile plants resulted in the production of fully male sterile plants which were characterized by the complete absence of pollen. Such plants were found to exhibit cytoplasmic male sterility as well as atrazine tolerance and to be totally homozygous recessive with respect to nuclear fertility restoring genes. In the absence of the usual dominant fertility restoring genes the cytoplasm uniformly manifests male sterility in addition to the atrazine herbicide tolerance. The agronomic properties have been improved through well known backcross techniques. Such plants exhibit cytoplasmic atrazine tolerance when applied as a foliar spray at a rate of 2 kilograms per hectacre.

We have found that suitable *Brassica napus* maintainer plants may be developed from the Bronowski cultivar since this source of germ plasm has been found as previously indicated to be highly variable with respect to the recessive genes for fertility restoration. For instance, individual Bronowski plants were sampled for the presence of recessive fertility restorer genes. Pollen from these individual plants was separately crossed onto completely male sterile plants, and the resulting seed was grown out and evaluated for male sterility. Each Bronowski individual was also self-pollinated to provide a seed source when found to possess the capacity to maintain male sterility.

Alternatively, it has been found that suitable *Brassica napus* maintainer plants may be derived from the Westar cultivar. Such cultivar is recognized to be of considerable economic importance because of its superior agronomic characteristics. Pollen from individual plants of the Westar cultivar was separately crossed onto completely male sterile plants and it was found that a Westar plant could be isolated which caused partially male sterile progeny to be produced. This Westar plant was homozygous dominant for only one fertility restoring gene. Partially male sterile plants were then crossed as a pollen source with the Westar plant which was homozygous dominant for the fertility restoring gene serving as the seed parent. The progeny are self-pollinated and the seed is grown out and evaluated for the ability to maintain male steility. Those individuals which are homozygous recessive maintainers for the cytoplasmic male sterile plant may be isolated and preserved. When selfpollinated a source of maintainer seed is provided.

Once a *Brassica napus* maintainer plant is located tissue culture optionally may be employed to multiply it so that its characteristics can be confirmed on a larger scale. The *Brassica napus* maintainer plants located as described herein lack atrazine tolerance when applied as a foliar spray at a rate of 2 kilograms per hectare.

Suitable restorer plants for the male sterility of the above discussed *Brassica napus* plants are provided by substantially uniform rape plants from which variability has been substantially removed by plant breeding techniques such as selfing, and selection. The only requirement is that such plants be homozygous for the dominant fertility restorer genes. Accordingly, fully fertile progeny will result in all instances.

The process of the present invention offers the advantage of simple bulk planting of (1) cytoplasmic male sterile plants which exhibit cytoplasmic herbicide tolerance and (2) male fertile plants which are capable of pollinating the same which lack herbicide tolerance. The male fertile plants may be either maintainer plants or restorer plants as previously discussed. Conventional planting techniques may be employed while forming a random mixture of the two plants. There is no requirement that equal quantities of of the two seed types be employed. For instance, the seeds capable of forming the cytoplasmic male sterile and herbicide tolerant plants which serve as the seed parent commonly will be provided in the major amount. Accordingly, such seed will commonly comprise 60 to 80 percent or more of the total amount of seed planted. Accordingly, one male fertile plant can commonly pollinate more than one male sterile plant. As will be apparent to those skilled in the plant technology, the relative proportions of the two plant types should be adjusted so as to achieve the desired level of pollination on a consistent basis while utilizing the minimum quantity of male fertile plants.

When carrying out the process of the present invention respective parent plants which have overlapping flowering cycles should be selected. Additionally, the process of the present invention relies upon conventional modes of pollen transfer (e.g., pollen carrying insects such as bees and/or the wind). Also, conventional techniques for harvesting the subject crop may be employed.

In a preferred embodiment of the process following bulk planting in a first planting area of the two required plant components, the resulting plants may be grown to maturity and the resulting seed formed on each of the plant components harvested in bulk. At least a portion of the seed produced thereby may next be planted in a second planting area without segregation to yield new plants to which a herbicide is applied prior to pollination to yield a substantially uniform population of herbicide tolerant plants. If the male fertile plant component present in the first planting area was a restorer, seed formed on the plants in the second area may simply be harvested. In this instance the herbicide could be conveniently applied by the farmer in conjunction with a weed control program. However, in the embodiment wherein the plant component of the first planting area is a maintainer, one conveniently may grow in pollinating proximity to the plants remaining in the second planting area following herbicide application a substantially homogeneous population of restorer plants for the male fertility. The respective substantially homogeneous populations conveniently may take the form of alternating rows, strips, or blocks which are amenable to selective harvesting. Seed capable of forming a predetermined male fertile $F_1$ hybrid variety may then be selectively recovered from the cytoplasmic male sterile plants of the second planting area.

In a further preferred embodiment of the process wherein the herbicide is applied at the post-flowering stage to a two component mixture of randomly grown plants which include a maintainer and the resulting seed is harvested, this resulting seed may next be planted in pollinating proximity to restorer plants which pollinate the cytoplasmic male sterile plants. Such pollinating proximity may take the form of bulk planting or adjoining substantially homogeneous plant populations. If bulk planting is employed, the restorer plants may be eliminated by a herbicide following pollination so that selective harvest from the cytoplasmic male sterile plants is made possible. Alternatively, such pollinating proximity may be made possible by growing adjoining substantially homogeneous populations which may conveniently take the form of alternating rows, strips, or blocks which are amenable to selective harvesting. In this instance, seed also may be selectively harvested from the restorer plants.

The present invention provides for the first time the ability to form a *Brassica napus* seed product consisting of substantially homogeneous seeds which upon growth yield rape plants which exhibit a combination of cytoplasmic male sterility and cytoplasmic atrazine tolerance when applied as a foliar spray at a rate of 2 kilograms per hectare. Alternatively, substantially homogeneous binary admixtures of seeds may be formed wherein the above is present with either a homozygous recessive maintainer for cytoplasmic male sterility or a homozygous dominant restorer for male fertility which each lack such atrazine tolerance. In such binary admixtures the seeds capable of forming male fertile plants are provided in a concentration sufficient to substantially completely pollinate the male fertile plants following germination and pollination.

Although the invention has been described with preferred embodiments, it is to be understood that variations and modifications may be resorted to as will be apparent to those skilled in the art. Such variations and modifications are to be considered within the purview and scope of the claims appended hereto.

We claim:

1. An improved process for forming a substantially homogeneous population of plants of a predetermined hybrid variety of a crop which is capable of undergoing both self-pollination and cross-pollination comprising:
    (a) growing in a first planting area a substantially random population of (1) cytoplasmic male sterile plants which exhibit cytoplasmic herbicide tolerance, and (2) male fertile plants which are capable of pollinating said cytoplasmic male sterile plants and which lack cytoplasmic herbicide tolerance, whereby said cytoplasmic male sterile plants (1) and said male fertile plants (2) are pollinated with pollen derived from said male fertile plants and seed is formed on said cytoplasmic male sterile plants and on said male fertile plants,
    (b) harvesting in bulk said seed which is formed on said plants of said first planting area,
    (c) growing at least a portion of the seed from step (b) in a second planting area in the absence of segregation between the seed derived from said cytoplasmic male sterile plants which exhibit cytoplasmic herbicide tolerance and said male fertile plants which lack cytoplasmic herbicide tolerance, and
    (d) contacting substantially all of the plants present in said second growing area prior to pollination with a herbicide which is effective to destroy said plants resulting from seed formed on said male fertile plants of said first planting area, whereby a substantially homogeneous population of a predetermined hybrid variety is formed which resulted from seed formed on said male sterile plants of said first planting area.

2. An improved process for forming a substantially homogeneous population of plants of a predetermined hybrid variety of a crop according to claim 1 wherein said crop is selected from the group consisting of grain crops, forage crops seed propagated fruits, seed propagated ornamentals, and industrial species.

3. An improved process for forming a substantially homogeneous population of plants of a predetermined hybrid variety of crop according to claim 1 wherein said crop is of the family Brassicaceae.

4. An improved process for forming a substantially homogeneous population of plants of a predetermined hybrid variety of crop according to claim 1 wherein said crop is of the genus Brassica.

5. An improved process for forming a substantially homogeneous population of plants of a predetermined hybrid variety of crop according to claim 1 wherein said crop is *Brassica napus*.

6. An improved process for forming a substantially homogeneous population of plants of a predetermined hybrid variety of crop according to claim 1 wherein said crop is *Brassica campestris*.

7. An improved process for forming a substantially homogeneous population of plants of a predetermined hybrid variety of crop according to claim 1 wherein said male fertile plants (2) are homozygous recessive maintainer plants for said cytoplasmic male sterile plants (1)

8. An improved process for forming a substantially homogeneous population of plants of a predetermined variety of hybrid crop according to claim 1 wherein said male fertile plants (2) are homozygous dominant fertility plants for said cytoplasmic male sterile plants (1).

9. An improved process for forming a substantially homogeneous population of plants of a predetermined variety of hybrid crop according to claim 1 wherein said male fertile plants (2) are homozygous dominant fertility restorer plants for said cytoplasmic male sterile plants (1) and said resulting plants of step (d) are male fertile $F_1$ hybrid plants, and which includes the additional step of (e) harvesting seed which forms on said male fertile $F_1$ hybrid plants as a result of self-pollination.

10. An improved process for forming a substantially homogeneous population of plants of a predetermined variety of hybrid seed crop according to claim 1 wherein said male fertile plants (2) are homozygous recessive maintainer plants for said cytoplasmic male sterile plants (1) and said resulting plants of step (d) are cytoplasmic male sterile plants, and which includes the additional steps of (e) growing in pollinating proximity to the substantially homogeneous population plants of step (d) a substantially homogeneous population of homozygous dominant fertility restorer plants for said cytoplasmic male sterile plants whereby said cytoplasmic male sterile plants of step (d) are pollinated with pollen from said restorer plants, and (f) harvesting seed from said cytoplasmic male sterile plants which is capable of forming a predetermined male fertile $F_1$ hybrid variety in the substantial absence of seed from said population of restorer plants 11. An improved process for forming a substantially homogeneous population of plants of a predetermined hybrid variety of crop according to claim 1 wherein said pollination takes place with the aid of pollen carrying insects.

12. An improved process for forming a substantially homogeneous population of plants of a predetermined hybrid variety of crop according to claim 1 wherein said herbicide operates by inhibiting photosynthesis.

13. An improved process for forming a substantially homogeneous population of plants of a predetermined hybrid variety of crop according to claim 1 wherein said herbicide is selected from the group consisting of s-triazines and as-triazines.

14. An improved process for forming a substantially homogeneous population of plants of a predetermined hybrid variety of crop according to claim 1 wherein said herbicide is atrazine.

15. An improved process for forming a substantially homogeneous population of plants of a predetermined hybrid variety of crop according to claim 1 wherein said herbicide is cyanazine.

16. An improved process for producing seed capable of forming a predetermined hybrid variety of a crop which is capable of undergoing both self-pollination and cross-pollination comprising:

(a) growing in a planting area a substantially random population of (1) cytoplasmic male sterile plants which exhibit cytoplasmic herbicide tolerance, and (2) male fertile plants which are capable of pollinating said cytoplasmic male sterile plants and which lack cytoplasmic herbicide tolerance, whereby said cytoplasmic male sterile plants (1) are pollinated with pollen derived from said male fertile plants (2), (b) contacting substantially all of the plants present in said growing area following said pollination with a herbicide which is effective to destroy said male fertile plants and which is ineffective to destroy said cytoplasmic male sterile plants, and (c) harvesting seed from said cytoplasmic male sterile plants which is capable of forming said hybrid plants in the substantial absence of seed from said male fertile plants which initially grew in said planting area.

17. An improved process for producing seed capable of forming a predetermined hybrid variety of a crop according to claim 16 wherein said crop is selected from the group consisting of grain crops, forage crops, seed propagated fruits, seed propagated ornamentals, and industrial species.

18. An improved process for producing seed capable of forming a predetermined hybrid variety of crop according to claim 16 wherein said crop is of the family Brassicaceae.

19. An improved process for producing seed capable of forming a predetermined hybrid variety of crop according to claim 16 wherein said crop is of the genus Brassica.

20. An improved process for producing seed capable of forming a predetermined hybrid variety of crop according to claim 16 wherein said crop is *Brassica napus*.

21. An improved process for producing seed capable of forming a predetermined hybrid variety of crop according to claim 16 wherein said crop is *Brassica campestris*.

22. An improved process for producing seed capable of forming a predetermined hybrid variety of crop according to claim 16 wherein said male fertile plants (2) are homozygous recessive maintainer plants for said cytoplasmic male sterile plants (1).

23. An improved process for producing seed capable of forming a predetermined variety of hybrid crop according to claim 16 wherein said male fertile plants (2) are homozygous dominant fertility restorer plants for said cytoplasmic male sterile plants (1).

24. An improved process for producing seed capable of forming a predetermined hybrid variety of crop according to claim 16 wherein said male fertile plants (2) are homozygous recessive maintainer plants for said cytoplasmic male sterile plants (1) and wherein said process includes the additional steps of (d) growing at least a portion of said seed from step (c) which is capable of forming plants which are cytoplasmic male sterile plants and which exhibit cytoplasmic herbicide tolerance in pollinating proximity to plants which are a homozygous dominant fertility restorer for said cytoplasmic male sterile plants whereby said cytoplasmic male sterile plants are pollinated with pollen derived from said restorer plants, and (e) selectively harvesting the seed which is formed on said cytoplasmic male sterile plants.

25. An improved process for producing seed capable of forming a predetermined hybrid variety of crop according to claim 24 wherein in step (d) said cytoplasmic male sterile plants are grown in at least one substantially uniform population adjacent at least one substantially uniform population of said restorer plants.

26. An improved process for producing seed capable of forming a predetermined hybrid variety of a crop according to claim 24 wherein in step (d) said cytoplasmic male sterile plants and said restorer plants are grown in a substantially random population, and said plants are contacted with a herbicide which selectively destroys said restorer plants following pollination of said cytoplasmic male sterile plants and prior to harvest step (e).

27. An improved process for producing seed capable of forming a predetermined hybrid variety of crop according to claim 16 wherein said pollination takes place with the aid of pollen carrying insects.

28. An improved process for producing seed capable of forming a predetermined hybrid variety of crop according to claim 16 wherein said herbicide operates by inhibiting photosynthesis.

29. An improved process for producing seed capable of forming a predetermined hybrid variety of crop according to claim 16 wherein said herbicide is selected from the group consisting of s-triazines and as-triazines.

30. An improved process for producing seed capable of forming a predetermined hybrid variety of crop according to claim 16 wherein said herbicide is atrazine.

31. An improved process for producing seed capable of forming a predetermined hybrid variety of crop according to claim 16 wherein said herbicide is cyanazine.

32. A *Brassica napus* seed product consisting of a substantially homogeneous assemblage of seeds which upon growth yield rape plants which exhibit a combination of cytoplasmic male sterility and cytoplasmic atrazine tolerance when applied as a foliar spray at a rate of 2 kilograms per hectare.

33. A *Brassica napus* seed product consisting of a substantially homogeneous binary admixture of seeds which upon growth yield
  (1) a first rape plant component which exhibits cytoplasmic male sterility and cytoplasmic atrazine tolerance when applied as a foliar spray at a rate of 2 kilograms per hectare, and
  (2) a second rape plant component which is capable of pollinating said first rape plant component, is a homozygous recessive maintainer for said cytoplasmic male sterility of the first rape plant component, and which lacks atrazine tolerance when applied as a foliar spray at a rate of 2 kilograms per hectare.

34. A *Brassica napus* seed product consisting of a substantially homogeneous binary admixture of seeds which upon growth yield
  (1) a first rape plant component which exhibits cytoplasmic male sterility and cytoplasmic atrazine tolerance when applied as a foliar spray at a rate of 2 kilograms per hectare, and
  (2) a second rape plant component which is capable of pollinating said first rape plant component, is a homozygous dominant fertility restorer for said first rape plant component, and which lacks atrazine tolerance when applied as a foliar spray at a rate of 2 kilograms per hectare.

* * * * *